(12) United States Patent
La Fortune

(10) Patent No.: US 7,073,373 B2
(45) Date of Patent: Jul. 11, 2006

(54) ABSORBENT STRUCTURE HAVING ENHANCED INTAKE PERFORMANCE CHARACTERISTICS AND METHOD FOR EVALUATING SUCH CHARACTERISTICS

(75) Inventor: Jeffrey M. La Fortune, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 410 days.

(21) Appl. No.: 10/720,867

(22) Filed: Nov. 24, 2003

(65) Prior Publication Data

US 2005/0113772 A1    May 26, 2005

(51) Int. Cl.
    *G01N 5/02*     (2006.01)
    *D04H 1/00*     (2006.01)
(52) U.S. Cl. .............................. 73/73; 73/38; 604/358; 442/414
(58) Field of Classification Search .................... 73/38, 73/73; 442/414; 604/358
    See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,777,073 A | 10/1988 | Sheth |
| 5,349,845 A * | 9/1994 | Blom ............................ 73/38 |
| 5,562,646 A | 10/1996 | Goldman et al. |
| 5,599,335 A | 2/1997 | Goldman et al. |
| 5,645,542 A | 7/1997 | Anjur et al. |
| 5,669,894 A | 9/1997 | Goldman et al. |
| 5,820,973 A | 10/1998 | Dodge, II et al. |
| 5,836,929 A | 11/1998 | Bewick-Sonntag et al. |
| 5,843,063 A | 12/1998 | Anderson et al. |
| 5,843,575 A | 12/1998 | Wang et al. |
| 5,849,405 A | 12/1998 | Wang et al. |
| 5,879,343 A | 3/1999 | Dodge, II et al. |
| 6,083,211 A | 7/2000 | DesMarais |
| 6,152,904 A | 11/2000 | Matthews et al. |

(Continued)

FOREIGN PATENT DOCUMENTS

WO    WO 91/14415 A1    10/1991

(Continued)

OTHER PUBLICATIONS

International Search Report and Written Opinion for PCT/US2004/007670 date Sep. 16, 2004, 5 pages.

*Primary Examiner*—Hezron Williams
*Assistant Examiner*—Rodney Frank
(74) *Attorney, Agent, or Firm*—Senniger Powers

(57) ABSTRACT

An absorbent structure is constructed of hydrophilic fibers and superabsorbent material and has a permeability as determined by an Absorbent Structure Permeability Test and a normalized retention capacity as determined by a Retention Capacity Test. The absorbent structure has an intake factor of at least about 3 wherein the intake factor is defined as the absorbent structure permeability divided by the normalized retention capacity. In another embodiment, the absorbent structure is constructed at least in part of a superabsorbent material and has an intake factor of at least about 3 and less than about 50.

31 Claims, 7 Drawing Sheets

U.S. PATENT DOCUMENTS

| | | |
|---|---|---|
| 6,392,116 B1 | 5/2002 | Beihoffer et al. |
| 6,441,266 B1 | 8/2002 | Dyer et al. |
| 6,506,960 B1 | 1/2003 | Young et al. |
| 2002/0115971 A1 | 8/2002 | Holmes et al. |
| 2002/0165509 A1 | 11/2002 | Baer et al. |
| 2003/0114807 A1 | 6/2003 | Underhill et al. |
| 2004/0214499 A1* | 10/2004 | Qin et al. .................. 442/414 |

FOREIGN PATENT DOCUMENTS

| | | |
|---|---|---|
| WO | WO 02/084024 A1 | 10/2002 |

* cited by examiner

ABSORBENT STRUCTURE HAVING ENHANCED INTAKE PERFORMANCE CHARACTERISTICS AND METHOD FOR EVALUATING SUCH CHARACTERISTICS

BACKGROUND OF THE INVENTION

This invention relates generally to absorbent structures used in disposable articles such as diapers, children's training pants, feminine care articles, incontinence articles, bandages, and the like, and more particularly to such absorbent structures having enhanced liquid intake performance characteristics and to the evaluation and characterization of the liquid intake performance of such absorbent structures.

Conventional disposable articles typically include an absorbent structure, also sometimes referred to as an absorbent core or absorbent composite, formed by air-forming, air-laying or other known forming technique. For example, the manufacture of such an absorbent structure may begin by fiberizing a fibrous sheet of hydrophilic material in a fiberizer or other shredding or comminuting device to form discrete fibers. In addition, particles or fibers of superabsorbent material, which are water insoluble, water swellable and capable of absorbing up to at least about ten times their weight in 0.9 weight percent sodium chloride solution in water (saline solution), are mixed with the discrete fibers. The hydrophilic fibers and superabsorbent material are then entrained in an air stream and directed to a foraminous forming surface upon which the fibers and superabsorbent material are deposited and accumulated to form the absorbent structure.

There is a continuing effort by absorbent structure manufacturers to improve the liquid intake performance of absorbent structures to thereby reduce the tendency of such a structure to leak as it becomes increasingly saturated during use, particularly where the structure is subjected to repeated liquid insults before being discarded. For example, one means of reducing the leakage of absorbent structures has been the extensive use of superabsorbent materials. Recent trends in commercial absorbent structure design have generally been focused on using a higher concentration of superabsorbent material and less fiber in an effort to make the absorbent structure thinner and more dense.

However, notwithstanding the increase in total absorbent capacity obtained by increasing the concentration of superabsorbent material, such absorbent structures may still leak during use. The leakage may be in part the result of the structure having an insufficient intake rate, e.g., the rate at which a liquid insult can be taken into and entrained within the structure for subsequent absorption by the superabsorbent material. More particularly, the intake rate of such absorbent structures may decrease upon repeated insults thereof due to the tendency of the superabsorbent material within the structure to swell as it absorbs and thus restrict or otherwise block the open channels between superabsorbent particles, or between the particles and the hydrophilic fibers within the absorbent structure. This phenomenon is often referred to as a form of gel-blocking and may occur as a result of the superabsorbent material lacking sufficient gel integrity or reaching such a high degree of swelling that it tends to be easily deformable under an external pressure, such as those loads applied by a wearer during movement or upon sitting down. The deformation under load causes the superabsorbent particles to block the open channels within the absorbent structure.

The intake rate of an absorbent structure upon repeated insults thereof is thus considered to be a key parameter for evaluating the in-use liquid intake performance of a disposable article incorporating such an absorbent structure. To date, research into improving the intake rate of absorbent structures has generally focused on the permeability of the absorbent structure, with the general belief that increasing the absorbent structure permeability will lead to increased liquid intake rates. However, the relationship between absorbent structure permeability and the intake rate of an absorbent structure upon repeated insults thereof may be informal at best and absorbent structure permeability, by itself, may be a sometimes inaccurate or otherwise inconsistent evaluating tool or predictor of the intake rate of an absorbent structure. This may be due to the fact that absorbent structure permeability is typically measured with the absorbent structure in a fully saturated state—a condition which rarely occurs for absorbent structures in actual use.

There is a need, therefore, for absorbent structures having enhanced intake performance characteristics, and for a more reliable means of evaluating and predicting the intake performance characteristics of absorbent structures, and more particularly for evaluating and predicting the intake rate of such absorbent structures upon repeated insults thereof.

SUMMARY OF THE INVENTION

In general, an absorbent structure according to one embodiment of the present invention comprises a mixture of hydrophilic fibers and superabsorbent material. The absorbent structure has a permeability as determined by an Absorbent Structure Permeability Test and a normalized retention capacity as determined by a Retention Capacity Test. The absorbent structure has an intake factor of at least about 3 wherein the intake factor is defined as the absorbent structure permeability divided by the normalized retention capacity.

In another embodiment, an absorbent structure generally comprises at least in part a superabsorbent material. The absorbent structure has a permeability as determined by an Absorbent Structure Permeability Test and a normalized retention capacity as determined by a Retention Capacity Test. The absorbent structure has an intake factor of at least about 3 and less than about 50 wherein the intake factor is defined as the absorbent structure permeability divided by the normalized retention capacity.

In one embodiment, an absorbent article of the present invention generally comprises a liner adapted for contiguous relationship with the body of the wearer. An outer cover is in superposed relationship with the liner and an absorbent body is disposed therebetween. The absorbent body comprises at least in part an absorbent structure having a permeability as determined by an Absorbent Structure Permeability Test and a normalized retention capacity as determined by a Retention Capacity Test. The absorbent structure has an intake factor of at least about 3 and less than about 50 wherein the intake factor is defined as the absorbent structure permeability divided by the normalized retention capacity.

In general, a method according to one embodiment of the present invention for rating the liquid intake performance of an absorbent structure generally comprises conducting an Absorbent Structure Permeability Test to determine a permeability of the absorbent structure and conducting a Retention Capacity Test to determine a retention capacity of the absorbent structure. An intake factor of the absorbent structure is determined wherein the intake factor defines a rating indicative of at least one liquid intake performance characteristic of the absorbent structure. The intake factor determining step comprises dividing the absorbent structure permeability by the retention capacity.

Other features of the invention will be in part apparent and in part pointed out hereinafter.

Definitions

Within the context of this specification, each term or phrase below will include the following meaning or meanings:

"Bonded-Carded" refers to webs that are made from fibers which are sent through a combing or carding unit, which separates or breaks apart and aligns the fibers in the machine direction to form a generally machine direction-oriented fibrous non-woven web. This material may be bonded together by methods that include point bonding, through air bonding, ultrasonic bonding, adhesive bonding or other suitable bonding technique.

"Hydrophilic" describes a material or surface which is wetted by aqueous liquids in contact therewith. The degree of wetting can, in turn, be described in terms of the contact angles and the surface tensions of the liquids and materials involved. Equipment and techniques suitable for measuring the wettability of particular materials or surfaces can be provided by a Cahn SFA-222 Surface Force Analyzer System, or a substantially equivalent system. When measured with this system, materials or surfaces having contact angles less than 90 degrees are designated "wettable" or hydrophilic, and those having contact angles greater than 90 degrees are designated "nonwettable" or hydrophobic.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al, which is incorporated herein by reference. Meltblown fibers are microfibers which may be continuous or discontinuous, are generally about 0.6 denier or smaller, and are generally self bonding when deposited onto a collecting surface.

"Non-woven" or "non-woven web" refers to materials or webs that are formed without the aid of a textile weaving or knitting process. The structure comprises individual or groups of fibers or threads which are interlaid, but not in an identifiable manner as in a knitted fabric. Non-woven structures have been formed from many processes such as, for example, meltblowing processes, spunbonding processes, and bonded-carded processes.

"Spunbond" refers to small diameter fibers which are formed by extruding molten thermoplastic material as filaments from a plurality of fine capillaries of a spinneret having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers of about 0.3 or larger, more particularly, between about 0.6 and about 10.

"Superabsorbent" refers to a water-swellable, water-insoluble organic or inorganic material capable, under the most favorable conditions, of absorbing at least about 10 times its weight and, more suitably, at least about 30 times its weight in an aqueous solution containing 0.9 weight percent sodium chloride solution in water.

"Thermoplastic" describes a material that softens when exposed to heat and which substantially returns to a non-softened condition when cooled to room temperature.

DETAILED DESCRIPTION

Figure 1:
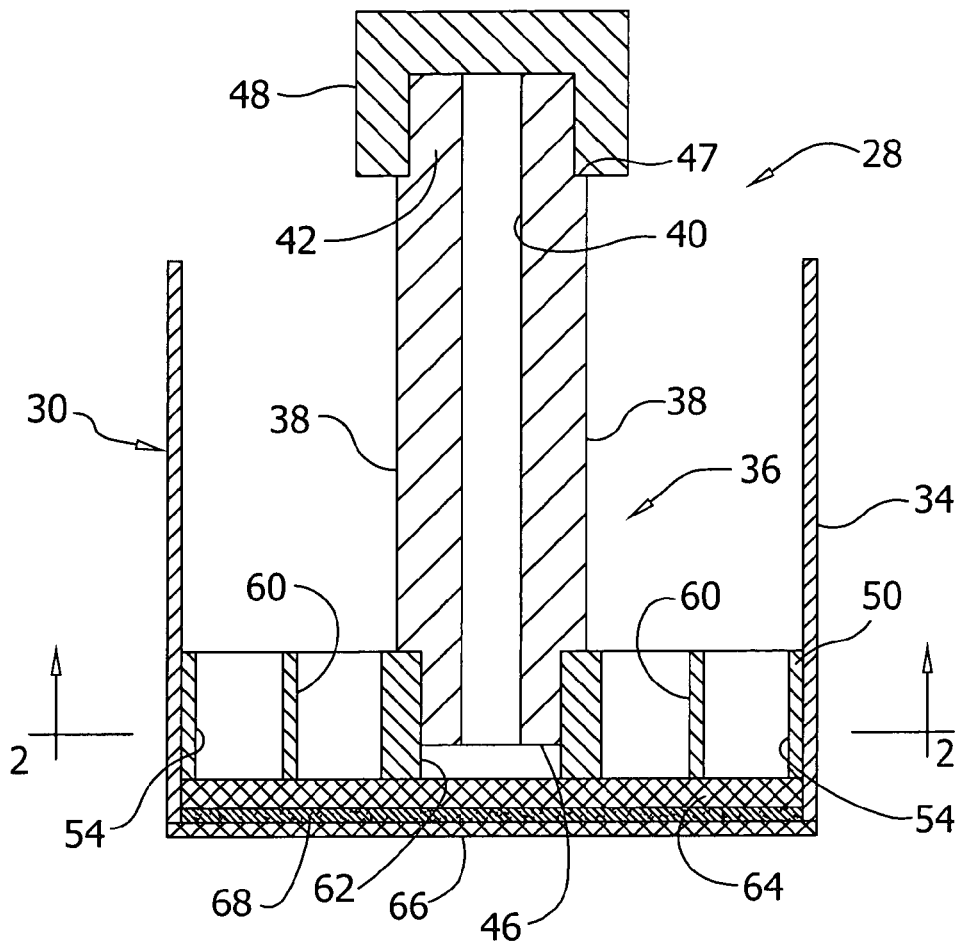
FIG. 1 is a cross-section of apparatus for conducting an Absorbent Structure Permeability Test.

The present invention is directed generally to absorbent structures having enhanced liquid intake performance characteristics, and more particularly to absorbent structures having an enhanced intake rate upon repeated liquid insults thereof. The present invention is also directed generally to methods for evaluating and comparing the liquid intake performance capabilities of various absorbent structures independent of shape, size, basis weight, density, material composition, concentration of materials within the absorbent structure and other parameters. It is understood that absorbent structures produced or evaluated in accordance with the present invention have a variety of uses. For example, possible uses include incorporation into a disposable or otherwise absorbent article for absorbing various liquid body exudates. Such articles are well known and can include, without limitation, feminine care pads, interlabial products, tampons, diapers, incontinence articles, training pants, bed pads, sweat absorbing pads, shoe pads, bandages, helmet liners, wipes, etc. As another example, the absorbent structure may be useful by itself, such as in the form of a tissue, towel, napkin or the like.

In one embodiment, the absorbent structure is a non-woven web comprising hydrophilic fibers and superabsorbent material. Examples of suitable hydrophilic fibers include naturally occurring organic fibers composed of intrinsically wettable material, such as cellulosic fibers. Suitable sources of cellulosic fibers include: wood fibers, such as bleached kraft softwood or hardwood, high-yield wood fibers, and ChemiThermoMechanical Pulp fibers; bagasse fibers; milkweed fluff fibers; wheat straw; kenaf; hemp; pineapple leaf fibers; or peat moss. Other hydrophilic fibers, such as regenerated cellulose and curled chemically stiffened cellulose fibers may also be densified to form absorbent structures that can expand to a higher loft when wetted. Pulp fibers may also be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids.

Suitable superabsorbent materials include natural, biodegradable, synthetic and modified natural polymers and materials. In addition, the superabsorbent materials can be inorganic materials, such as silica gels, or organic compounds such as cross-linked polymers. The term "cross-linked" used in reference to the superabsorbent material refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces. Examples of synthetic superabsorbent polymers include the alkali metal and ammonium salts of poly(acrylic acid) and poly (methacrylic acid), poly(acrylamides), poly (vinyl ethers), maleic anhydride copolymers with vinyl ethers and alpha-olefins, poly(vinyl pyrrolidone), poly(vinylmorpholinone), poly(vinyl alcohol), and mixtures and copolymers thereof.

The superabsorbent material used in making the absorbent structure is suitably in the form of discrete particles. Superabsorbent particles can be of any suitable shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of superabsorbent material may also be used in the absorbent structure. The superabsorbent materials may be in various length and cross-sectional dimensions and may also be in various degrees of neutralization.

The absorbent structure may be formed in any conventional manner, such as by being air-formed, air-laid, bonded-carded or formed by other known techniques in which fibers and superabsorbent material are commingled to form a non-woven web. The absorbent structure may be of substantially any shape and size suitable for its intended purpose. The absorbent structure may also comprise two or more non-woven webs or layers, which may be positioned in side-by-side relationship or surface-to-surface relationship, and all or a portion of adjacent webs or layers may be secured together to form the absorbent structure.

The superabsorbent material is suitably homogeneously mixed with the hydrophilic fibers to provide a uniform distribution of the superabsorbent material and fibers throughout the absorbent structure. Alternatively, the superabsorbent material can be distributed non-uniformly within the absorbent structure, such as across the width, along the length and/or through the thickness of the structure to define discrete target regions or zones of the structure within which the superabsorbent material is located. The concentration of superabsorbent material within the absorbent structure can also be non-uniform through all or part of the thickness, across all or part of the width and/or along all or part of the length of the absorbent structure. In general, the concentration of superabsorbent material within the absorbent structure is suitably about 90 weight percent or less based on the total weight of the absorbent structure, but is in any event greater than zero. In one embodiment, the concentration of superabsorbent material within the absorbent structure is more suitably in the range of about 30 to about 80 weight percent.

The absorbent structure may or may not be wrapped or otherwise encompassed by a suitable tissue wrap for maintaining the integrity and/or shape of the absorbent structure.

The absorbent structure also has certain liquid intake performance characteristics, including absorbent structure permeability, retention capacity and intake rate, which are measurable using the tests described below.

Absorbent Structure Permeability Test

The following test is used to determine the permeability of the absorbent structure, and more particularly a "z-direction" permeability of the absorbent structure based on liquid flow through the thickness of the structure. The test is conducted at under what is commonly referred to as "free swell" conditions. The term "free swell" means that the superabsorbent material in the absorbent structure is allowed to swell without a swell restraining load applied thereto upon absorbing test solution.

Figure 2:
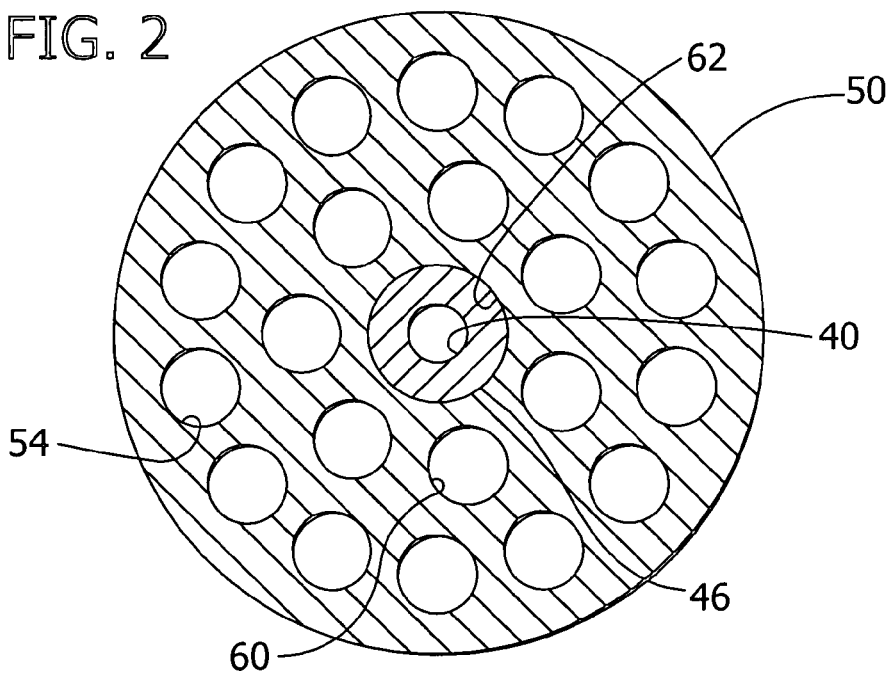
FIG. 2 is a section taken in the plane of line 2—2 of FIG. 1.

A suitable Permeability Test apparatus is shown in FIGS. 1 and 2 and indicated generally in FIG. 1 as 28. The test apparatus comprises a sample container, generally indicated at 30, and a piston, generally indicated at 36. The piston 36 comprises a cylindrical LEXAN shaft 38 having a concentric cylindrical hole 40 bored down the longitudinal axis of the shaft. Both ends of the shaft 38 are machined to provide upper and lower ends respectively designated 42, 46. A weight, indicated as 48, rests on one end 42. A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 400 mesh stainless steel screen 64. A suitable screen 64 material is part number 85385T972 from McMaster-Carr Supply of Chicago, Ill., U.S.A.

The sample container 30 comprises a cylinder 34 and a 100 mesh stainless steel cloth screen 66 that is biaxially stretched to tautness and attached to the lower end of the cylinder prior to attachment. A suitable material for the screen 66 is part number 85385T976 from McMaster-Carr Supply, a company having offices in Chicago, Ill., U.S.A. An absorbent structure sample, indicated as 68 in FIG. 1, is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm and a height of approximately 10 cm. The cylinder 34 includes a set of drainage holes (not shown) or other suitable means for holding a fluid level in the sample container at approximately 7.8 cm above the screen 66. The piston head 50 is machined from a LEXAN rod or equivalent material and has a height of approximately 16 mm and a diameter sized such that it fits within the cylinder 34 with minimum wall clearance but still slides freely. The shaft 38 is machined from a LEXAN rod or equivalent material and has an outer diameter of about 2.32 cm and an inner diameter of about 0.64 cm.

The shaft upper end 42 is approximately 2.54 cm long and approximately 1.52 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of 0.9 weight percent saline solution. The combined weight of the piston 36 and annular weight 48 equals approximately 596 grams (g), which corresponds to a pressure applied to the absorbent structure sample 68 of about 0.3 pounds per square inch (psi), or about 20.7 dynes/cm$^2$, over a sample area of about 28.27 cm$^2$.

When test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the Absorbent Structure Permeability Test, the piston 36, with the weight 48 seated thereon, is placed in an empty sample container 30 and the height from the bottom of the weight to the top of the cylinder 34 is measured using a caliper or suitable gauge accurate to 0.01 mm. It is important to measure the height of each sample container 30 empty and to keep track of which piston 36 and weight 48 is used when using multiple test apparatus. The same piston 36 and weight 48 should be used for measurement when the absorbent structure sample 68 is later swollen following saturation.

A circular absorbent structure sample 68 (e.g., either formed or otherwise cut from a larger absorbent structure), with the tissue wrap removed and having a cross-sectional diameter of about 6 cm is placed in the sample container 30 at the bottom of the cylinder 34 in contact with the screen 64. The sample container 30 is submerged in a test solution comprising 0.9 weight percent saline solution for a time period of about 60 minutes to saturate the sample 68. Without the piston 36 and weight 48 assembly on the sample during saturation, the superabsorbent material within the sample is allowed to swell without a restraining load being applied thereto (e.g., under free swell conditions). After 60 minutes, the piston 36 and weight 48 assembly is placed on the saturated sample 68 in the sample container 30 and then the sample container 30, piston 36, weight 48, and sample 68 are removed from the test solution. The thickness of the saturated sample 68 is determined by again measuring the height from the bottom of the weight 48 to the top of the cylinder 34, using the same caliper or gauge used previously provided that the zero point is unchanged from the initial height measurement. The height measurement obtained from measuring the empty sample container 30, piston 36, and weight 48 is subtracted from the height measurement obtained after saturating the absorbent structure sample 68. The resulting value is the thickness, or height "H" of the saturated sample 68.

The absorbent structure permeability measurement is initiated by delivering a flow of test solution into the sample container 30 with the saturated sample 68, piston 36, and weight 48 inside. The flow rate of test solution into the container 30 is adjusted to maintain a fluid height of about 7.8 cm above the bottom of the sample container. The quantity of test solution passing through the sample 68 versus time is measured gravimetrically. Data points are collected every second for at least twenty seconds once the fluid level has been stabilized to and maintained at about 7.8 cm in height. The flow rate Q through the swollen sample 68 is determined in units of grams/second (g/s) by a linear least-square fit of fluid passing through the sample 68 (in grams) versus time (in seconds).

Permeability in square microns is obtained by the following equation:

$$K=[Q*H*Mu*10^8]/[A*Rho*P]$$

where K=Permeability (cm$^2$), Q=flow rate (g/sec), H=height of sample (cm), Mu=liquid viscosity (poise) (approximately one centipoise for the test solution used with this Test), A=cross-sectional area for liquid flow (cm$^2$), Rho=liquid density (g/cm$^3$) (approximately one g/cm$^3$, for the test solution used with this Test) and P=hydrostatic pressure (dynes/cm$^2$) (normally approximately 3,923 dynes/cm$^2$). The hydrostatic pressure is calculated from $$P=Rho*g*h$$

where Rho=liquid density (g/cm$^3$), g=gravitational acceleration, nominally 981 cm/sec$^2$, and h=fluid height, e.g., 7.8 cm for the Absorbent Structure Permeability Test described herein.

Four samples of an absorbent structure are tested and the results are averaged to determine the absorbent structure permeability.

Gel Bed Permeability Test

A Gel Bed Permeability Test measures the permeability of the superabsorbent material itself (e.g., separate from the formed absorbent structure). This test is substantially similar to the Absorbent Structure Permeability Test set forth above, with the following noted exceptions. Instead of an absorbent structure sample 68 being placed in the cup, a 0.9 grams weight sample of the superabsorbent material being tested is prepared by prescreening the superabsorbent particles through a U.S. standard 30 mesh screen and retaining the particles on a U.S. standard 50 mesh screen. As a result, the test sample comprises particles sized in the range of about 300 to about 600 microns. The particles can be prescreened by hand or automatically. The sample is placed in the sample container 30 and the container is then submerged in the test solution for a time period of about 60 minutes to saturate and swell the superabsorbent material under free swell conditions. The same height measurements obtained for the Absorbent Structure Permeability Test are taken, e.g., with the container 30 empty and with the superabsorbent material within the container and saturated.

The gel-bed permeability measurement is initiated by delivering a flow of test solution into the sample container 30 with the saturated superabsorbent material, the piston 36, and the weight 48 inside. The test solution flow rate is adjusted to maintain a fluid height of about 4 cm (instead of the 7.8 cm used for the Absorbent Structure Permeability Test) above the bottom of the sample container. The quantity of test solution passing through the superabsorbent material versus time is measured gravimetrically. Data points are collected every second for at least twenty seconds once the fluid level has been stabilized to and maintained at about 4 cm in height. The flow rate Q through the superabsorbent material is determined in units of grams/second (g/s) by a linear least-square fit of fluid passing through the container (in grams) versus time (in seconds). The gel bed permeability of the superabsorbent material is then determined using the equation set forth above for the Absorbent Structure Permeability Test (noting that the fluid height is now 4.0 cm instead of 7.8 cm).

Liquid Saturation Retention Capacity Test

Figure 3:
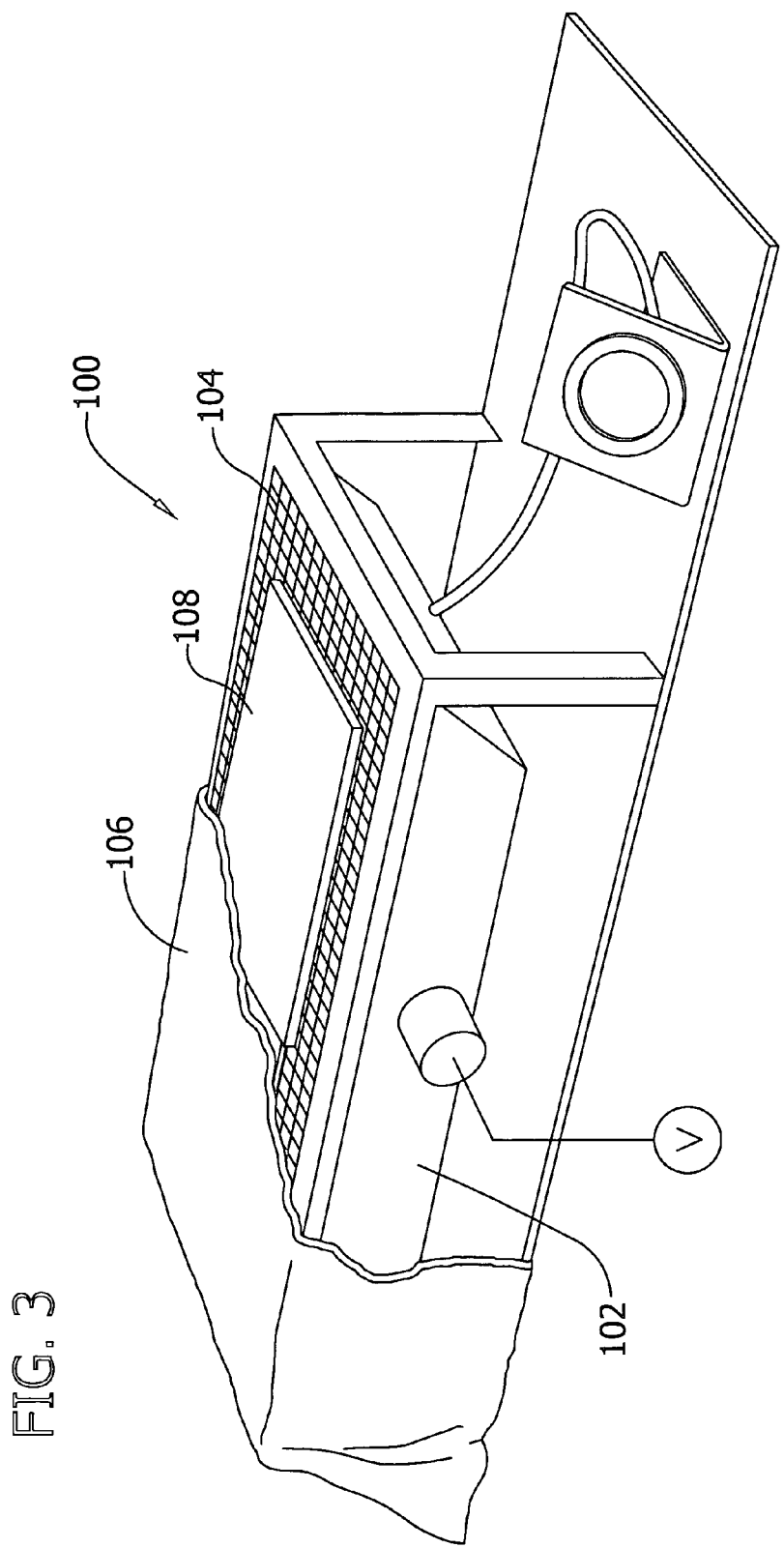
FIG. 3 is a cross-section of apparatus for conducting a Liquid Retention Capacity Test.

The following test is used to determine a retention capacity of an absorbent structure, i.e., the capacity of the absorbent structure for retaining liquid therein. An absorbent structure sample 108 having length and width dimensions of approximately four inches by four inches (approximately 10.16 cm by 10.16 cm) is weighed with the tissue wrap material on and the weight in grams is recorded. The sample 108 is then wrapped in toweling (not shown), such as Scott Hi-Dri available from Kimberly-Clark of Neenah, Wis., U.S.A., and submerged in an excess quantity of test solution (i.e., 0.9 weight percent saline solution at about 23 degrees Celsius) for twenty minutes. After this time period, the sample 108 is removed from the test solution and placed on a retention capacity test apparatus, indicated generally at 100 in FIG. 3, comprising a vacuum box 102, a TEFLON fiberglass screen 104 having 0.25 inch (0.6 cm) openings and supported by the vacuum box, and a flexible rubber cover 106 sized for overlaying the screen on the vacuum box.

More particularly, the absorbent structure sample 100 (with toweling) is placed uncovered (e.g., by the rubber cover 106) on the screen 104 and allowed to drip dry for about one minute. The rubber cover 106 is then placed over the sample 100 and screen 104 (e.g., to generally form a seal over the vacuum box 102) and a vacuum (V) of about 0.5 pounds/square inch (about 34.5 dynes/square cm) is drawn on the vacuum box (and hence the sample) for a period of about five minutes. The sample 100 is then removed from the toweling, making an effort to recover loose fibers and superabsorbent particles along with the sample. The recovered sample is again weighed and the weight in grams is recorded. A "total retention capacity" of the sample is determined by subtracting the dry weight of the sample from the weight of the recovered sample after application of the vacuum and is recorded as grams of liquid retained. For relative comparisons to absorbent structures of different mass, a "normalized retention capacity" is determined as the total retention capacity divided by the dry weight of the sample and is recorded as grams of liquid retained per gram of absorbent structure (g/g, or $g_{liq}/g_{abs}$.).

If absorbent structure fibers and/or superabsorbent material are drawn through the fiberglass screen into the vacuum box during testing, a screen having smaller openings should be used and the test should be re-done. Alternatively, a piece of tea bag material or other similar material can be placed between the sample and the screen and the total retention capacity adjusted for the liquid retained by the tea bag or other material.

At least three samples of each absorbent structure are tested and the results are averaged to provide the retention capacity (e.g., total and normalized retention capacity) of the absorbent structure.

Fluid Intake Evaluation Test

Figure 4:
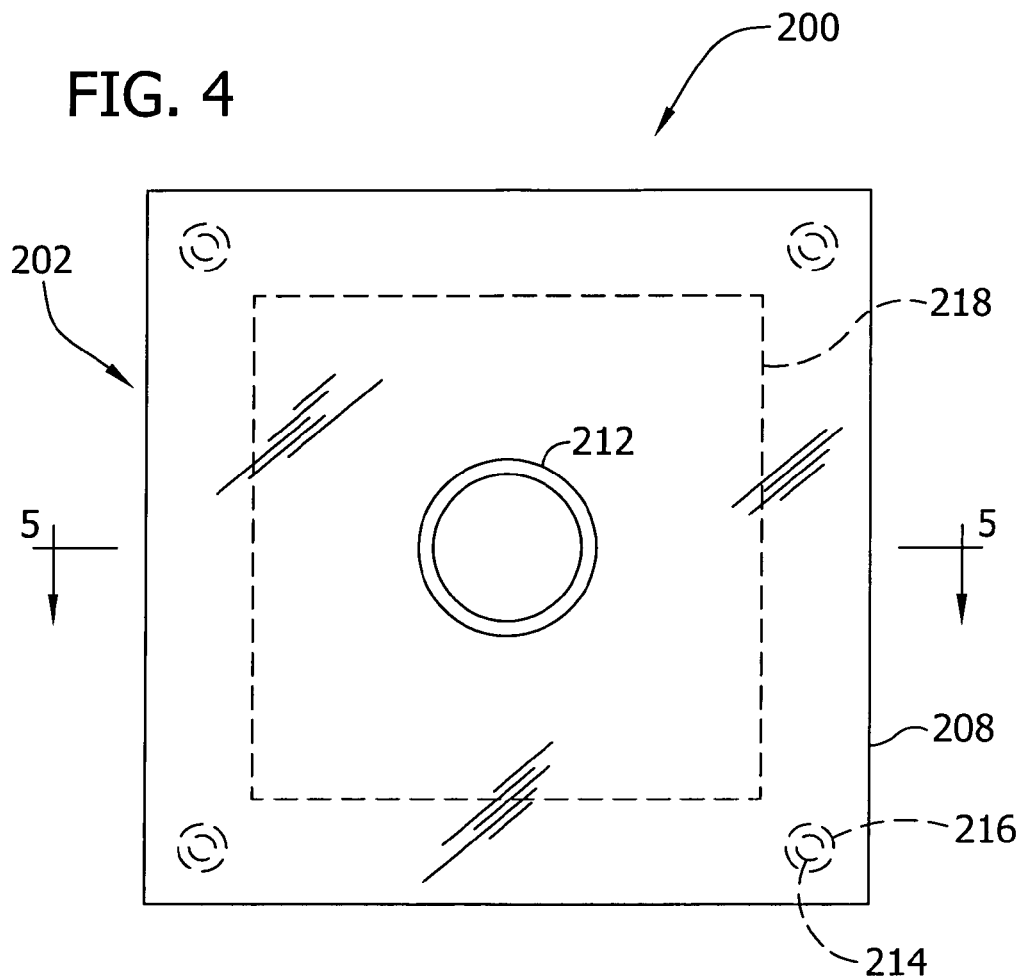
FIG. 4 is a top plan of apparatus for conducting a Fluid Intake Evaluation Test.
Figure 5:
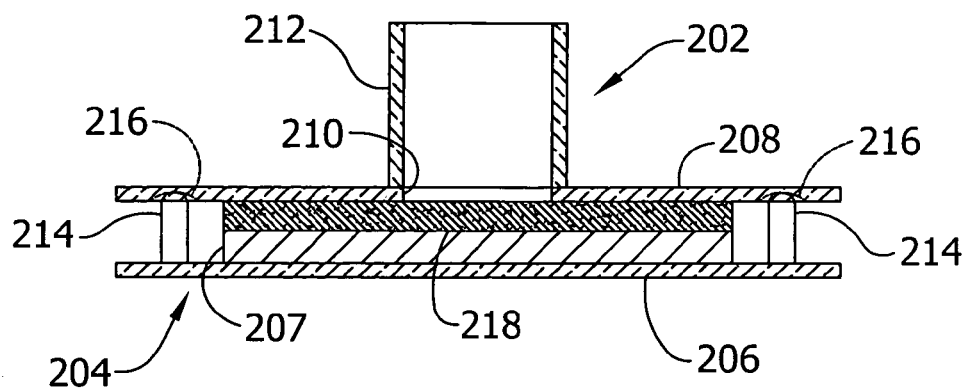
FIG. 5 is a section taken in the plane of line 5—5 of FIG. 4.

The Fluid Intake Evaluation (FIE) Test determines the amount of time required for an absorbent structure, and more particularly a sample thereof, to take in (but not necessarily absorb) a known amount of test solution (0.9 weight percent saline solution). A suitable apparatus for performing the FIE Test is shown in FIGS. 4 and 5 and is generally indicated at 200. The test apparatus 200 comprises upper and lower assemblies, generally indicated at 202 and 204 respectively. The lower assembly 204 comprises a generally 7 inch by 7 inch (45 cm by 45 cm) square plate 206 constructed of a transparent material such as plexiglass and a generally 4.5 inch (11.4 cm) by 4.5 inch (11.4 cm) square platform 207 centered on the plate for centering the absorbent structure sample during the test.

The upper assembly 202 comprises a generally square plate 208 constructed similar to the lower plate 206 and having a central opening 210 formed therein. A cylinder 212 having an inner diameter of about one inch is secured to the upper plate 208 at the central opening 210 and extends upward substantially perpendicular to the upper plate. The central opening 210 of the upper plate 208 should have a diameter at least equal to the inner diameter of the cylinder 212 where the cylinder is mounted on top of the upper plate. However, the diameter of the central opening 210 may instead be sized large enough to receive the outer diameter of the cylinder 212 within the opening so that the cylinder is secured to the upper plate 208 within the central opening.

Pin elements 214 are located near outside corners of the lower plate 206, and corresponding recesses 216 in the upper plate 208 are sized to receive the pin elements to properly align and position the upper assembly 202 on the lower plate during testing. The weight of the upper assembly 202 (e.g., the upper plate 208 and cylinder 212) is suitable for simulating approximately 0.05 pounds/square inch (psi), or about 3.45 dynes/square cm, pressure on the absorbent structure sample during the FIE Test.

To run the FIE Test, an absorbent structure sample 218 having length and width dimensions of about four inches by about four inches (about 10.16 cm by about 10.16 cm) is weighed, with the tissue wrap on, and the weight is recorded in grams. The sample 218 is then centered on the lower plate 206 of the test apparatus 200 and the upper assembly 202 is placed over the sample in opposed relationship with the lower plate, with the pins 214 of the lower plate seated in the recesses 216 formed in the upper plate 208 and the cylinder 212 generally centered over the sample. A test solution (0.9 weight percent saline solution) is prepared with a small amount of blue dye added thereto. A first predetermined amount of the test solution (e.g., to simulate a first insult of the absorbent structure), corresponding to approximately 30 percent of the total retention capacity of the absorbent structure as determined by the Retention Capacity Test set forth above, is poured into a beaker. The test solution is then poured into the top of the cylinder 212 and allowed to flow down into the absorbent structure sample 218. A stopwatch is started when the first drop of solution contacts the sample 218 and is stopped when the liquid ring between the edge of the cylinder 212 and the sample disappears. The reading on the stopwatch is recorded to two decimal places and represents the intake time (in seconds) required for the first insult to be taken into the absorbent structure sample 218.

A time period of fifteen minutes is allowed to elapse, after which a second insult equal to the first insult (e.g., to simulate a second insult of the absorbent structure to cumulatively achieve approximately 60 percent of the total retention capacity of the structure) is poured into the top of the cylinder 212 and again the intake time is measured as described above. After an additional fifteen minutes, the procedure is repeated for a third insult, also equal to the first insult, e.g., to simulate a third insult of the absorbent structure to cumulatively achieve approximately 90 percent of the total retention capacity of the structure.

An intake rate (e.g., in milliliters/second) for each of the three insults is determined by dividing the amount of liquid for each insult by the intake time measured for the corresponding insult.

While the FIE Test as described above is typically conducted with the tissue wrap on the absorbent structure sample, in instances where the intake rate is expected to exceed about 6 ml/sec, the tissue wrap of the portion of the sample which faces the upper plate of the test apparatus should be removed and replaced with a flexible plastic screen having a mesh size of about 18 openings per inch to avoid impeding the flow of solution into the sample.

At least six samples of each absorbent structure are subjected to the FIE Test and the results are averaged to determine the intake time and intake rate of the absorbent structure.

Experiment

Absorbent structure samples having different absorbent structure permeabilities and retention capacities were made in a laboratory air-forming apparatus and subjected to the Absorbent Structure Permeability Test, Retention Capacity Test and FIE Test to evaluate the relationship between the absorbent structure permeability, retention capacity and intake rate of absorbent structures upon repeated insults thereof. Each of the absorbent structure samples comprised one of two different hydrophilic fibers. Fiber I, available from Bowater of Coosa Pines, Ala., U.S.A under the designation CR-1654, has a fiber permeability (as determined by subjecting an airlaid structure comprising only the fibers and having a basis weight of about 600 grams/square meter and a density of about 0.2 grams/cubic centimeter to the Absorbent Structure Permeability Test) of about 35 square microns. The second fiber, Fiber II, is a cellulosic fiber chemically cross-linked to form intrafiber crosslinks, such as disclosed in PCT Publication No. WO 02/084024 A1 entitled Cross-Linked Pulp and Method of Making Same, and has a fiber permeability (as determined by subjecting an airlaid structure comprising only the fibers and having a basis weight of about 600 grams/square meter and a density of about 0.2 grams/cubic centimeter to the Absorbent Structure Permeability Test) of about 75 square microns.

Each of the absorbent structure samples also comprised one of three different types of superabsorbent material (SAM). Type I, available from Dow Chemical Company of Midland, Mich., U.S.A. under the tradename DRYTECH 2035M, has a relatively low gel bed permeability (as determined by the Gel Bed Permeability Test set forth previously), e.g., of about four square microns; Type II is available from Stockhausen, Inc. of Greensboro, N.C., U.S.A., under the designation SXM 9543 and has a higher gel bed permeability, such as about 40 square microns as determined by the Gel Bed Permeability Test; and Type III is a superabsorbent material available from Stockhausen, Inc. under the designation 1284 and has a gel bed permeability of approximately 140 square microns as determined by the Gel Bed Permeability Test.

Four different combinations of the hydrophilic fibers and superabsorbent materials were used to form absorbent structures (using a laboratory airforming device) as set forth in Table 1 below. For each absorbent structure composition, three different type samples were formed for testing, designated in Table 1 by the letters a, b and c, with the concentration of superabsorbent material respectively being about 30 percent, about 43.5 percent or about 60 percent by weight of the absorbent structure sample. The target basis weight of each absorbent structure sample formed by the laboratory airforming device was approximately 600 grams per square meter (gsm) and the target density of each sample was about 0.2 grams/cubic centimeter (g/cc).

The normalized retention capacity of each absorbent structure sample was determined using the Retention Capacity Test described previously and recorded in Table 1 below.

TABLE 1

| Absorbent Structure Sample | SAM | Fiber | Target SAM Concentration (percent) | Basis Weight (gsm) | Density (g/cc) | Retention Capacity (g/g) |
|---|---|---|---|---|---|---|
| 1a | Type I | Fiber II | 30.0 | 606.8 | 0.208 | 13.49 |
| 1b | Type I | Fiber II | 43.5 | 619.8 | 0.204 | 17.09 |
| 1c | Type I | Fiber II | 60.0 | 626.9 | 0.221 | 19.18 |
| 2a | Type II | Fiber I | 30.0 | 603.2 | 0.213 | 13.44 |
| 2b | Type II | Fiber I | 43.5 | 611.8 | 0.206 | 15.62 |
| 2c | Type II | Fiber I | 60.0 | 584.5 | 0.236 | 17.87 |
| 3a | Type III | Fiber I | 30.0 | 635.2 | 0.226 | 11.94 |
| 3b | Type III | Fiber I | 43.5 | 631.9 | 0.220 | 13.39 |
| 3c | Type III | Fiber I | 60.0 | 634.2 | 0.321 | 16.03 |
| 4a | Type III | Fiber II | 30.0 | 603.5 | 0.199 | 12.68 |
| 4b | Type III | Fiber II | 43.5 | 618.5 | 0.223 | 14.23 |
| 4c | Type III | Fiber II | 60.0 | 618.1 | 0.215 | 17.47 |

Additional absorbent structure samples were cut from the crotch region of each of three different commercially available diapers, including one sample (sample 5) cut from a HUGGIES® Supreme diaper and two samples cut from HUGGIES® UltraTrim diapers (one sample (sample 6) having a lower density than the other sample (sample 7)), all of which are available from Kimberly-Clark Worldwide, Inc. of Neenah, Wis. These absorbent structure samples were cut from the crotch area of the respective diaper and comprise the Fiber 1 hydrophilic fibers and a 43.5 weight percent concentration of the Type II superabsorbent material. The normalized retention capacity of each of these samples was measured using the Retention Capacity Test set forth previously and is recorded in Table 2 below.

TABLE 2

| Sample | SAM | Fiber | Target SAM Concentration (percent) | Basis Weight (gsm) | Density (g/cc) | Retention Capacity (g/g) |
|---|---|---|---|---|---|---|
| 5 | Type II | Fiber I | 43.5 | 956.5 | 0.175 | 13.92 |
| 6 | Type II | Fiber I | 43.5 | 1049.5 | 0.225 | 14.69 |
| 7 | Type II | Fiber I | 43.5 | 1023.0 | 0.254 | 14.12 |

The Absorbent Structure Permeability Test and FIE Test set forth previously were also conducted for each of the absorbent structure samples and the results are shown in Table 3 below.

TABLE 3

| Absorbent Structure Sample | Retention Capacity (g/g) | Z-Dir Permeability ($\mu^2$) | Intake Rate (ml/sec) | | |
|---|---|---|---|---|---|
| | | | First | Second | Third |
| 1a | 13.49 | 35.6 | 2.87 | 3.90 | 2.73 |
| 1b | 17.09 | 23.2 | 2.95 | 3.35 | 2.42 |
| 1c | 19.18 | 11.7 | 2.11 | 1.69 | 1.24 |
| 2a | 13.44 | 43.1 | 1.49 | 3.86 | 2.86 |
| 2b | 15.62 | 40.7 | 1.51 | 3.65 | 2.61 |
| 2c | 17.87 | 28.8 | 1.57 | 2.89 | 1.77 |
| 3a | 11.94 | 55.3 | 1.96 | 6.39 | 6.36 |
| 3b | 13.39 | 63.8 | 2.35 | 6.77 | 6.18 |
| 3c | 16.03 | 81.5 | 2.30 | 6.07 | 5.37 |
| 4a | 12.68 | 67.3 | 3.98 | 7.20 | 5.54 |
| 4b | 14.23 | 73.7 | 3.51 | 6.98 | 5.10 |
| 4c | 17.47 | 96.1 | 4.01 | 7.38 | 5.38 |
| 5 | 13.92 | 23.6 | 2.88 | 2.89 | 2.55 |
| 6 | 14.69 | 28.2 | 2.56 | 2.44 | 2.00 |
| 7 | 14.12 | 16.2 | 2.01 | 1.81 | 1.48 |

Figure 6A:
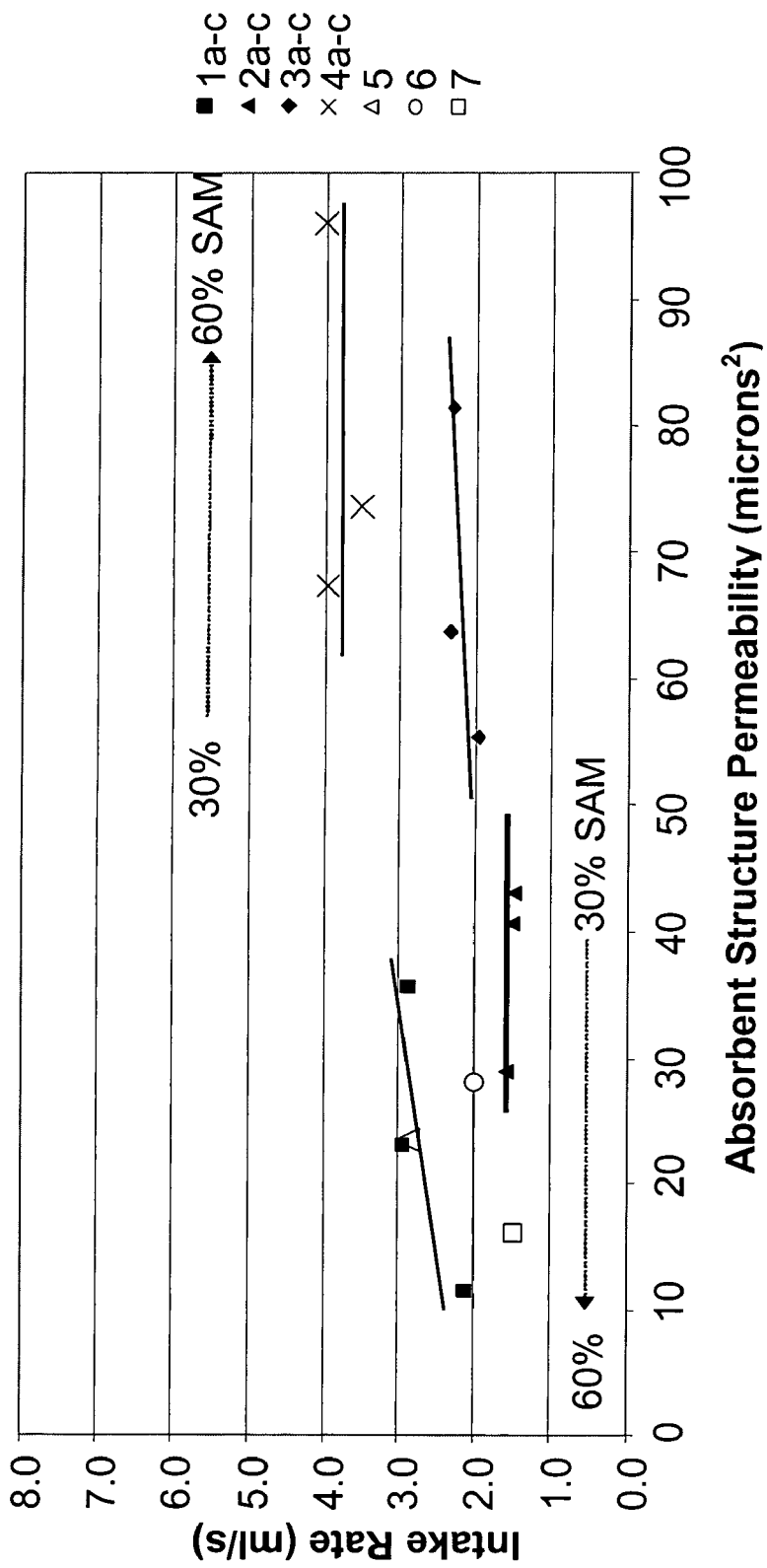
FIG. 6a is a plot of intake rate versus permeability for a first liquid insult of an absorbent structure.
Figure 6B:
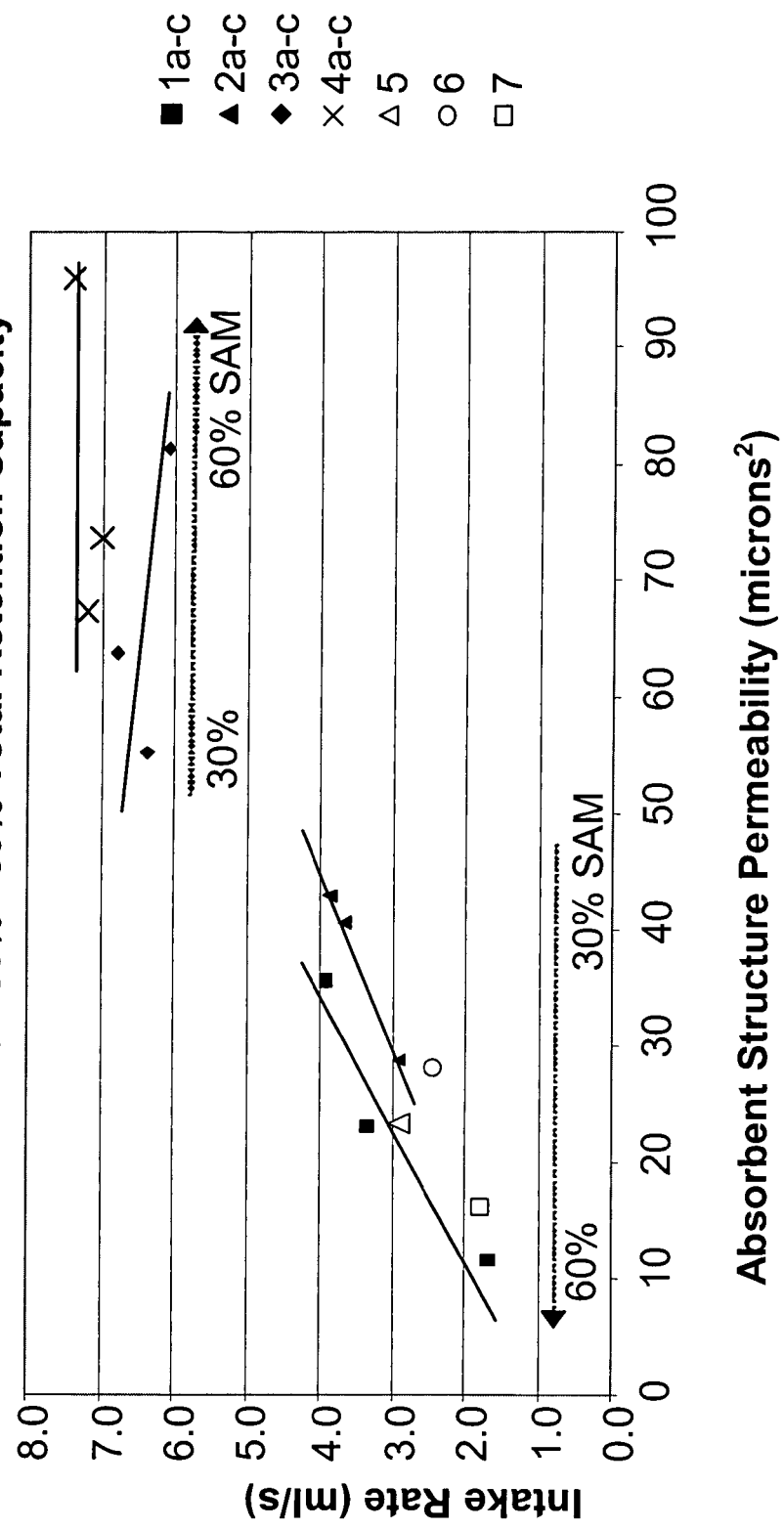
FIG. 6b is a plot of intake rate versus permeability for a second liquid insult of an absorbent structure.
Figure 6C:
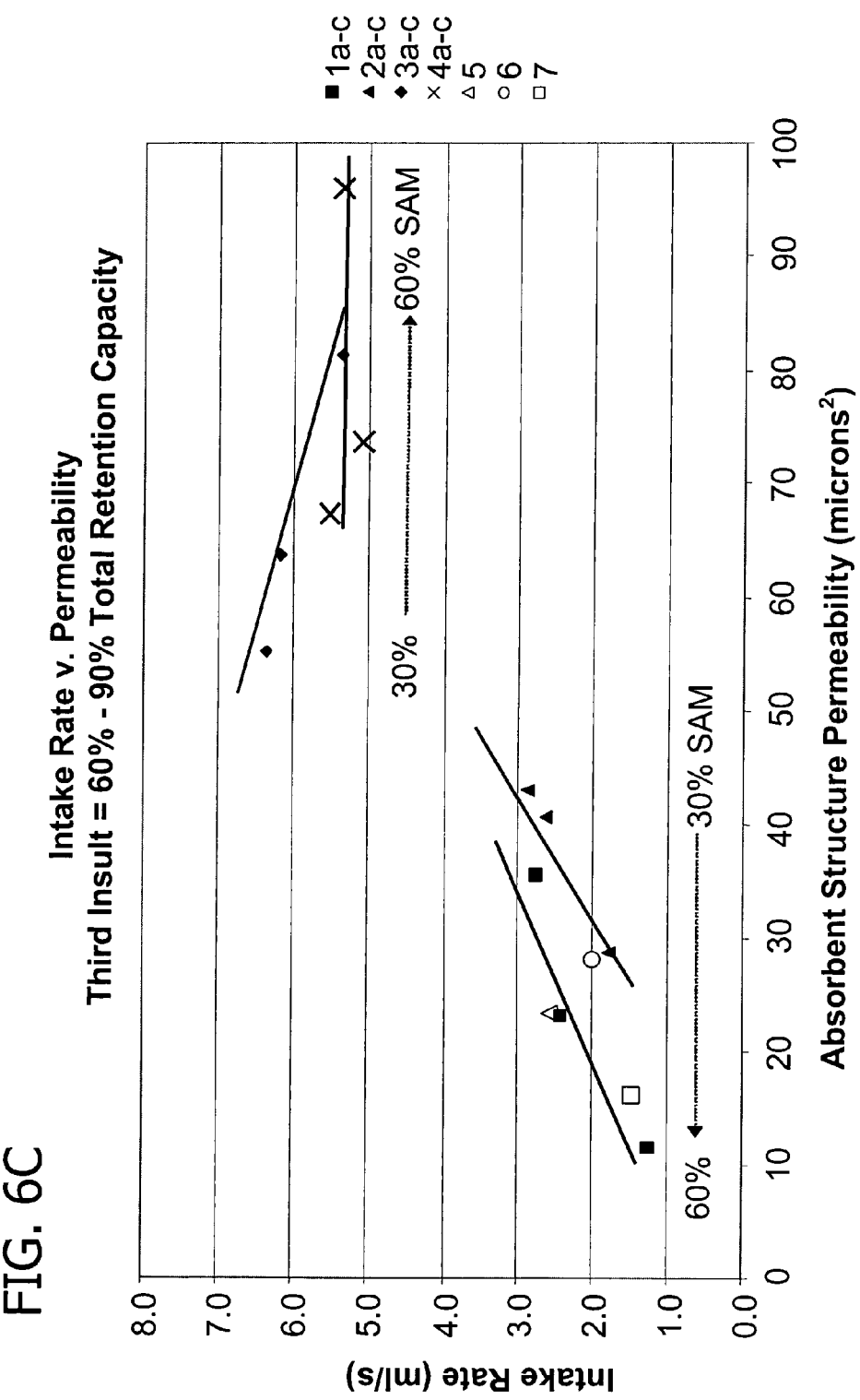
FIG. 6c is a plot of intake rate versus permeability for a third liquid insult of an absorbent structure.

FIGS. 6a, 6b and 6c are plots of absorbent structure permeability versus intake rate for the first, second and third insults of the FIE tests for each of the absorbent structure samples. As indicated by the direction arrows in each of the plots, the SAM concentration within each sample increases from right to left (i.e., the permeability decreases with an increase in SAM concentration) for absorbent structures 1 (samples 1a–c) and 2 (samples 2a–c). For absorbent structures 3 (samples 3a–c) and 4 (samples 4a–c) the SAM concentration within each sample increases from left to right (i.e., the permeability increased with the SAM concentration).

As shown particularly in FIGS. 6b and 6c, the absorbent structures having a higher absorbent structure permeability (e.g., structures 3 and 4) generally provided higher intake rates for the second and third insults than the absorbent structures having a lower absorbent structure permeability (e.g., structures 1, 2 and 5–7). However, the slopes defined by linear fitting the three data points obtained for each absorbent structure (e.g., samples a, b and c for each respective absorbent structure) are different for the different absorbent structures. More notably, the absorbent structures (e.g., structures 3 and 4) having a higher permeability tended to have a constant or even declining intake rate for second and third insults as the absorbent structure permeability increased. Consequently, reliance on the absorbent structure permeability as a sole predictor of the intake rate capabilities of an absorbent structure may at best be a generalization.

Figure 7:
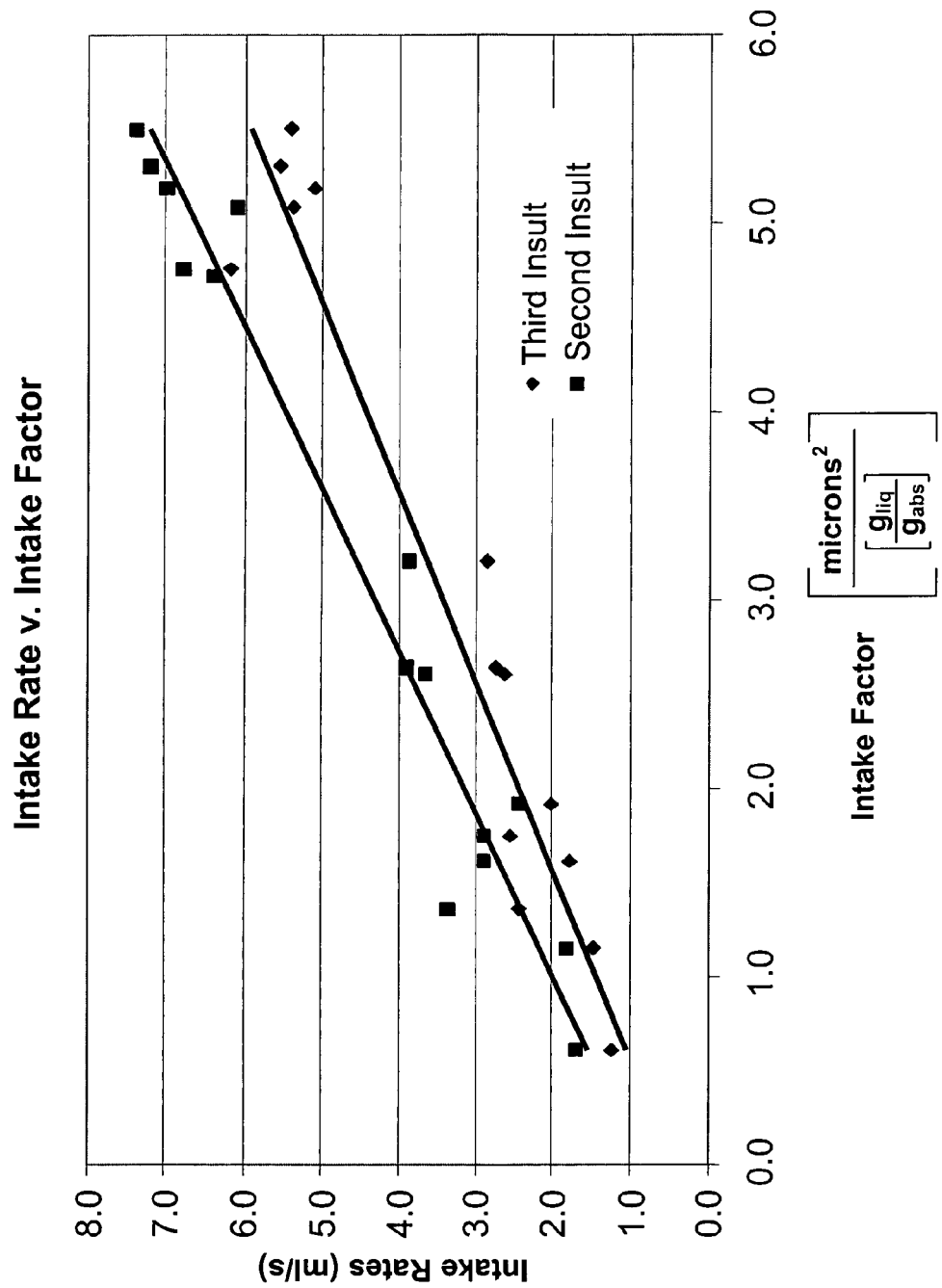
FIG. 7 is a plot of intake rate versus intake factor for second and third liquid insults of an absorbent structure.

To derive a more accurate and consistent means of evaluating and/or predicting the intake rate of an absorbent structure upon second and third insults thereof, a conventional statistical analysis software was used to further analyze the test data. For example, one suitable software is available from the SAS Institute of Cary, N.C., U.S.A. under the tradename JMP. A statistically linear correlation was determined between the intake rates for second and third insults, and an "intake factor" which is defined herein as the absorbent structure permeability as determined by the Absorbent Structure Permeability test set forth previously divided by the retention capacity of the absorbent structure, and more suitably the normalized retention capacity of the absorbent structure, as determined by the Retention Capacity Test set forth previously. FIG. 7 is a plot of the intake rates for the second and third insults of the tested absorbent structure samples versus the intake factor derived for each of the samples. As illustrated in the plot, the intake rate increases linearly with the intake factor for both the second and third insults.

More particularly, for a second insult equal to about 30% of the total retention capacity of the structure and corresponding cumulatively to about 60% of the total retention capacity, the intake rate of the absorbent structure is defined approximately by the following equation:

$$\text{Intake Rate} = 0.8326 + 1.1562 * \text{Intake Factor} \quad \text{(Eq. 1)}$$

where;

Intake Rate is in milliliters/second; and

Intake Factor is in square microns/(grams liquid/grams absorbent structure).

For a third insult equal to about 30% of the total retention capacity of the absorbent structure and corresponding cumulatively to about 90% of the total retention capacity, the intake rate of the absorbent structure is defined by the following equation:

$$\text{Intake Rate} = 0.8997 + 0.994 * \text{Intake Factor} \quad \text{(Eq. 2)}$$

where the Intake Rate and Intake Factor have the same units as set forth above for Eq. 1.

The absorbent structure samples (samples 5, 6 and 7) cut from the commercially available diapers had intake factors in the range of about 1.1 to about 2.0 for both the second and third insults, while intake factors of greater than five were achieved for some of the other absorbent structure samples (e.g., samples 3c and 4a–c).

In accordance with one embodiment of the present invention, the absorbent structure suitably has an intake factor (having the units square microns/(grams liquid/grams absorbent structure)) of about 3 or greater, more suitably of about 4 or greater, even more suitably an intake factor of about 5 or greater and still more suitably of about 5.5 or greater. In another embodiment, the absorbent structure has an intake factor of less than about 50, more suitably less than about 25, still more suitably less than about 10 and even more suitably in the range of about 5 to about 5.5.

The normalized retention capacity of the absorbent structure is suitably in the range of about 9 g/g to about 24 g/g, and more suitably in the range of about 12 g/g to about 20 g/g.

For a second insult of the absorbent structure equal to about 30 percent of the total saturation capacity of the structure and corresponding cumulatively to about 60 percent of the total saturation capacity, the intake rate of the absorbent structure is suitably about four milliliters per second or greater, more suitably about five milliliters per second or greater, even more suitably about six milliliters per second or greater, and still more suitably about seven milliliters per second or greater.

For a third insult equal to about 30 percent of the total saturation capacity and corresponding cumulatively to about 90 percent of the total saturation capacity, the intake rate of the absorbent structure is suitable about four milliliters per second or greater, more suitably about five milliliters per second or greater, and even more suitably about six milliliters per second or greater.

In view of the linear relationship between the intake factor and the intake rate of an absorbent structure, the intake factor provides an effective means for evaluating and comparing different absorbent structures irrespective of basis weight, density, material compositions and concentrations, as well as other parameters. For example, in one embodiment of a method for rating the intake performance capabilities of an absorbent structure, the absorbent structure permeability and the retention capacity of the absorbent structure are determined using, respectively, the Absorbent Structure Permeability Test and the Retention Capacity Test set forth previously. The intake factor is then determined as the absorbent structure permeability divided by the retention capacity of the absorbent structure and defines a rating which is indicative of the intake performance properties of the absorbent structure, and more particularly the intake performance properties for second and third insults of the absorbent structure. More suitably, the intake factor is determined as the absorbent structure permeability divided by the normalized retention capacity of the absorbent structure. However, it is understood that the intake factor may instead be determined as the absorbent structure permeability divided by the total retention capacity of the absorbent structure without departing from the scope of this invention.

In one embodiment of a method for comparing the intake performance capabilities of two or more absorbent structures, an intake factor is determined for each absorbent structure and used to compare, and thus predict, which of the compared absorbent structures is likely to provide better intake performance, and more particularly a higher intake rate, during repeated insults thereof.

The intake factor can also be used to construct an absorbent structure having desired intake performance characteristics, without the need for testing various absorbent structure compositions and constructions. More particularly, using the intake factor, and more particularly using the linear relationships defined above in Eqs. 1 and 2, an absorbent structure can be constructed to have a desired intake rate for a second and/or third insult of a desired amount of 0.9 weight percent saline solution.

EXAMPLE

A four inch by four inch (10.16 cm by 10.16 cm) absorbent structure is to be constructed wherein the absorbent structure has an intake rate of about 7 ml/sec for a second insult of 0.9 weight percent saline solution of about 50 milliliters (ml). Since the second insult corresponds to about thirty percent of the total retention capacity of the absorbent structure, a desired total retention capacity of the structure to be constructed is about 166.7 ml. Assuming that one milliliter of the saline solution weighs about 1 gram, the desired total retention capacity of the absorbent structure can be otherwise stated as 166.7 grams.

Using equation 1 above which defines the intake rate of an absorbent structure (for a second insult thereof) as a linear function of the intake factor, a target intake factor of about 5.35 is required to achieve the desired intake rate of about 7 ml/sec for the second insult. Over a range of target normalized retention capacities, such as between about 9 g/g and about 24 g/g, the corresponding permeability required to achieve the target intake factor can be determined by multiplying the normalized retention capacity by the required intake factor (e.g., 5.35). Alternatively, over a range of target absorbent structure permeabilities, the corresponding normalized retention capacity required to achieve the target intake factor can be determined by dividing the permeability by the intake factor. Table 4 below sets forth various normalized retention capacities and corresponding absorbent structure permeabilities which result in an intake factor of about 5.35.

TABLE 4

| Intake Factor | Retention Capacity (g/g) | Absorbent Structure Permeability ($\mu^2$) | Absorbent Structure Weight (g) | Basis Weight (gsm) |
|---|---|---|---|---|
| 5.35 | 9.0 | 48.1 | 18.5 | 1794.0 |
| 5.35 | 9.5 | 50.8 | 17.5 | 1699.6 |
| 5.35 | 10.0 | 53.5 | 16.7 | 1614.6 |

TABLE 4-continued

| Intake Factor | Retention Capacity (g/g) | Absorbent Structure Permeability ($\mu^2$) | Absorbent Structure Weight (g) | Basis Weight (gsm) |
|---|---|---|---|---|
| 5.35 | 10.5 | 56.2 | 15.9 | 1537.7 |
| 5.35 | 11.0 | 58.8 | 15.2 | 1467.8 |
| 5.35 | 11.5 | 61.5 | 14.5 | 1404.0 |
| 5.35 | 12.0 | 64.2 | 13.9 | 1345.5 |
| 5.35 | 12.5 | 66.9 | 13.3 | 1291.7 |
| 5.35 | 13.0 | 69.5 | 12.8 | 1242.0 |
| 5.35 | 13.5 | 72.2 | 12.3 | 1196.0 |
| 5.35 | 14.0 | 74.9 | 11.9 | 1153.3 |
| 5.35 | 14.5 | 77.6 | 11.5 | 1113.5 |
| 5.35 | 15.0 | 80.2 | 11.1 | 1076.4 |
| 5.35 | 15.5 | 82.9 | 10.8 | 1041.7 |
| 5.35 | 16.0 | 85.6 | 10.4 | 1009.1 |
| 5.35 | 16.5 | 88.3 | 10.1 | 978.5 |
| 5.35 | 17.0 | 90.9 | 9.8 | 949.8 |
| 5.35 | 17.5 | 93.6 | 9.5 | 922.6 |
| 5.35 | 18.0 | 96.3 | 9.3 | 897.0 |
| 5.35 | 18.5 | 99.0 | 9.0 | 872.7 |
| 5.35 | 19.0 | 101.6 | 8.8 | 849.8 |
| 5.35 | 19.5 | 104.3 | 8.5 | 828.0 |
| 5.35 | 20.0 | 107.0 | 8.3 | 807.3 |
| 5.35 | 20.5 | 109.7 | 8.1 | 787.6 |
| 5.35 | 21.0 | 112.3 | 7.9 | 768.8 |
| 5.35 | 21.5 | 115.0 | 7.8 | 751.0 |
| 5.35 | 22.0 | 117.7 | 7.6 | 733.9 |
| 5.35 | 22.5 | 120.4 | 7.4 | 717.6 |
| 5.35 | 23.0 | 123.0 | 7.2 | 702.0 |
| 5.35 | 23.5 | 125.7 | 7.1 | 687.1 |
| 5.35 | 24.0 | 128.4 | 6.9 | 672.7 |

For each target normalized retention capacity identified in Table 4, a target weight of the absorbent structure to be constructed is determined as the desired total retention capacity of the absorbent structure to be constructed (e.g., about 166.7 grams) divided by the target normalized retention capacity. For example, for a normalized retention capacity of about 12 g/g the target weight of the absorbent structure to be constructed (e.g., a four inch by four inch sample as is used in the FIE Test described herein) is about 13.9 grams. Once the target weight is determined, a target basis weight of the absorbent structure to be constructed is determined by dividing the target weight by the horizontal cross-sectional area (e.g., taken in the plane of the length and width dimensions) of the absorbent structure. For example, for the normalized retention capacity of about 12 g/g, the target basis weight is 13.9 g divided by 103.2 $cm^2$ (16 $in.^2$), or about 1,345.5 gsm.

The absorbent structure composition, material concentration, density and other design and construction parameters can then be selected to provide the target basis weight, normalized retention capacity and absorbent structure permeability.

While the above example illustrates construction of test sample absorbent structures having length and width dimensions of about four inches by four inches, it is understood that the absorbent structure to be constructed may be of any length and width dimensions, including non-uniform dimensions (e.g., a contoured or shaped structure) without departing from the scope of this invention. It is also contemplated that the absorbent structure constructed based on the intake factor, such as in the manner described in the above example, may be used only for a portion of a larger absorbent structure, such as for the crotch area of a diaper absorbent structure.

As described previously, the absorbent structure formed in accordance with the present invention may be incorporated in an absorbent article. As used herein, an absorbent article refers to an article which may be placed against or in proximity to the body of the wearer (e.g., contiguous to the body) to absorb and/or retain various waste discharged from the body. Some absorbent articles, such as disposable articles, are intended to be discarded after a limited period of use instead of being laundered or otherwise restored for reuse. In one embodiment, an absorbent article of the present invention comprises an outer cover, a bodyside liner positioned in facing relation with the outer cover and adapted for contiguous relationship with the body of the wearer, and an absorbent body disposed between the outer cover and the liner. The bodyside liner 51 may be generally coextensive with the outer cover 49, or may instead overlie an area which is larger or smaller than the area of the outer cover 49, as desired.

In one embodiment, the outer cover is stretchable and may or may not be somewhat elastic. More particularly, the outer cover is sufficiently extensible such that once stretched under the weight of the insulted absorbent body, the outer cover will not retract substantially back toward its original position. However, it is contemplated that the outer cover 49 may instead be generally non-extensible and remain within the scope of this invention.

The outer cover may be a single layer structure or it may be a multi-layered laminate structure to provide desired levels of extensibility as well as liquid impermeability and vapor permeability. For example, the outer cover can be a two-layer construction, including an outer layer constructed of a vapor permeable material and an inner layer constructed of a liquid impermeable material, with the two layers being secured together by a suitable laminate adhesive. The vapor permeable outer layer can be any suitable material and is desirably one which provides a generally cloth-like texture. Suitable materials for the outer layer include non-woven webs, woven materials and knitted materials. Non-woven fabrics or webs have been formed from many known processes, for example, bonded carded web processes, meltblowing processes and spunbonding processes.

The liquid impermeable inner layer of the outer cover can be either vapor permeable (i.e., "breathable") or vapor impermeable. The inner layer is desirably manufactured from a thin plastic film, although other flexible liquid impermeable materials may also be used. More particularly, the inner layer can be made from either cast or blown film equipment, can be coextruded and can be embossed if so desired. It is understood that the inner layer may otherwise be made from any suitable non-elastic polymer composition and may include multiple layers. Where the inner layer is vapor permeable, it may contain such fillers as micropore developing fillers, e.g. calcium carbonate; opacifying agents, e.g. titanium dioxide; and antiblock additives, e.g. diatomaceous earth. Suitable polymers for the inner layer include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

The bodyside liner is preferably pliable, soft feeling, and nonirritating to the wearer's skin, and is employed to help isolate the wearer's skin from the absorbent body. The liner is desirably less hydrophilic than the absorbent body to present a relatively dry surface to the wearer, and is sufficiently porous to be liquid permeable to thereby permit liquid to readily penetrate through its thickness. A suitable bodyside liner 51 may be manufactured from a wide selection of web materials. Various woven and nonwoven fabrics including either or both synthetic and natural fibers can be used for the liner 51. For example, the bodyside liner 51 may be composed of a meltblown or spunbonded web of the desired fibers, and may also be a bonded-carded-web. Layers of different materials that may have different fiber deniers can also be used. The various fabrics can be composed of natural fibers, synthetic fibers or combinations thereof.

The various components of the absorbent article are assembled together using a suitable form of attachment, such as adhesive, sonic bonds, thermal bonds or combinations thereof. For example, in one embodiment the outer cover and absorbent body are secured to each other with lines of adhesive, such as a hot melt or pressure-sensitive adhesive. The bodyside liner is also secured to the outer cover and may also be secured to the absorbent body using the same forms of attachment.

In accordance with the present invention, the absorbent body comprises at least in part an absorbent structure as described previously herein. It is contemplated that the absorbent body may comprise one or more than one of the absorbent structures, such as in overlaid or side-by-side relationship, and/or it may comprise one more layers in addition to the absorbent structure, such as a surge layer, without departing from the scope of this invention.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description shall be interpreted as illustrative and not in a limiting sense.

What is claimed is:

1. An absorbent structure comprising a mixture of hydrophilic fibers and superabsorbent material, the absorbent structure having a permeability as determined by an Absorbent Structure Permeability Test and a normalized retention capacity as determined by a Retention Capacity Test, said absorbent structure having an intake factor of at least about 3 wherein the intake factor is defined as the absorbent structure permeability divided by the normalized retention capacity.

2. An absorbent structure as set forth in claim 1 wherein the absorbent structure has an intake factor of less than about 50.

3. An absorbent structure as set forth in claim 1 wherein the absorbent structure has a total retention capacity as determined by the Retention Capacity Test and is capable of receiving at least a first, a second and a third insult of 0.9 weight percent saline solution wherein each insult corresponds to approximately thirty percent of the total retention capacity of the absorbent structure, said absorbent structure having an intake rate as determined by a FIE Test for at least one of the second and third insults of at least about four milliliters per second.

4. An absorbent structure as set forth in claim 3 wherein the absorbent structure has an intake rate as determined by a FIE Test for at least one of the second and third insults of at least about 5 milliliters per second.

5. An absorbent structure as set forth in claim 4 wherein the absorbent structure has an intake rate as determined by a FIE Test for each of the second and third insults of at least about 5 milliliters per second.

6. An absorbent structure as set forth in claim 1 wherein the hydrophilic fibers comprise cellulosic fibers.

7. An absorbent structure as set forth in claim 6 wherein the cellulosic fibers are chemically cross-linked to form intrafiber cross-links.

8. An absorbent structure as set forth in claim 1 wherein the superabsorbent material has a gel bed permeability of at least about 40 square microns as determined by a Gel Bed Permeability Test.

9. An absorbent structure as set forth in claim 1 where the superabsorbent material in the absorbent structure comprises in the range of about 30 percent to about 80 percent of the weight of the absorbent structure.

10. An absorbent structure as set forth in claim 1 wherein the normalized retention capacity of the absorbent structure as determined by the Retention Capacity Test is in the range of about 9 g/g to about 24 g/g.

11. An absorbent structure comprising at least in part a superabsorbent material, said absorbent structure having a permeability as determined by an Absorbent Structure Permeability Test and a normalized retention capacity as determined by a Retention Capacity Test, said absorbent structure having an intake factor of at least about 3 and less than about 50 wherein the intake factor is defined as the absorbent structure permeability divided by the normalized retention capacity.

12. An absorbent structure as set forth in claim 11 wherein the absorbent structure has an intake factor of less than about 10.

13. An absorbent structure as set forth in claim 11 wherein the absorbent structure has an intake factor in the range of about 3 to about 5.5.

14. An absorbent structure as set forth in claim 11 wherein the absorbent structure has a total retention capacity as determined by the Retention Capacity Test and is capable of receiving at least a first, a second and a third insult of 0.9 weight percent saline solution wherein each insult corresponds to approximately thirty percent of the total retention capacity of the absorbent structure, said absorbent structure having an intake rate as determined by a FIE Test for at least one of the second and third insults of at least about four milliliters per second.

15. An absorbent structure as set forth in claim 14 wherein the absorbent structure has an intake rate as determined by a FIE Test for at least one of the second and third insults of at least about 5 milliliters per second.

16. An absorbent structure as set forth in claim 15 wherein the absorbent structure has an intake rate as determined by a FIE Test for each of the second and third insults of at least about 5 milliliters per second.

17. An absorbent structure as set forth in claim 11 wherein the superabsorbent material has a gel bed permeability of at least about 40 square microns as determined by a Gel Bed Permeability Test.

18. An absorbent structure as set forth in claim 11 where the superabsorbent material in the absorbent structure comprises in the range of about 30 percent to about 80 percent of the weight of the absorbent structure.

19. An absorbent structure as set forth in claim 11 wherein the normalized retention capacity of the absorbent structure as determined by the Retention Capacity Test is in the range of about 9 g/g to about 24 g/g.

20. An absorbent article for personal wear, said absorbent article comprising:
a liner adapted for contiguous relationship with the body of the wearer;
an outer cover in superposed relationship with the liner; and
an absorbent body disposed between the liner and the outer cover, the absorbent body comprising at least in part an absorbent structure having a permeability as determined by an Absorbent Structure Permeability Test and a normalized retention capacity as determined by a Retention Capacity Test, said absorbent structure having an intake factor of at least about 3 and less than about 50 wherein the intake factor is defined as the absorbent structure permeability divided by the normalized retention capacity.

21. An absorbent structure as set forth in claim 20 wherein the absorbent structure has an intake factor of less than about 10.

22. An absorbent structure as set forth in claim 20 wherein the absorbent structure has an intake factor in the range of about 3 to about 5.5.

23. An absorbent structure as set forth in claim 20 wherein the absorbent structure has a total retention capacity as determined by the Retention Capacity Test and is capable of receiving at least a first, a second and a third insult of 0.9 weight percent saline solution wherein each insult corresponds to approximately thirty percent of the total retention capacity of the absorbent structure, said absorbent structure having an intake rate as determined by a FIE Test for at least one of the second and third insults of at least about four milliliters per second.

24. An absorbent structure as set forth in claim 23 wherein the absorbent structure has an intake rate as determined by a FIE Test for at least one of the second and third insults of at least about 5 milliliters per second.

25. An absorbent structure as set forth in claim 24 wherein the absorbent structure has an intake rate as determined by a FIE Test for each of the second and third insults of at least about 5 milliliters per second.

26. An absorbent article as set forth in claim 20 wherein the absorbent structure comprises a mixture of hydrophilic fibers and superabsorbent material.

27. An absorbent structure as set forth in claim 20 wherein the normalized retention capacity of the absorbent structure as determined by the Retention Capacity Test is in the range of about 9 g/g to about 24 g/g.

28. A method of rating the liquid intake performance of an absorbent structure, said method comprising:
conducting an Absorbent Structure Permeability Test to determine a permeability of the absorbent structure;
conducting a Retention Capacity Test to determine a retention capacity of the absorbent structure; and
determining an intake factor of the absorbent structure wherein the intake factor defines a rating indicative of at least one liquid intake performance characteristic of the absorbent structure, said intake factor determining step comprising dividing the absorbent structure permeability by the retention capacity.

29. A method as set forth in claim 28 wherein the retention capacity as determined by the Retention Capacity Test is a normalized retention capacity, said normalized retention capacity being defined as a total retention capacity of the absorbent structure as determined by the Retention Capacity Test divided by the weight of the absorbent structure.

30. A method as set forth in claim 28 wherein the absorbent structure is capable of receiving at least a first, a second and a third insult of 0.9 weight percent saline solution wherein each insult corresponds to approximately thirty percent of a total retention capacity of the absorbent structure as determined by the Retention Capacity Test, the intake factor defining a rating indicative of the intake rate of the absorbent structure as determined by a FIE Test for at least one of the second and third insults thereof.

31. A method as set forth in claim 30 wherein the intake rate of the absorbent structure as determined by the FIE test for at least one of the second and third insults is a linear function of the intake factor.

* * * * *